Jan. 21, 1964 M. L. NIES Plant Pat. 2,345
GRAPEVINE
Filed Aug. 29, 1961
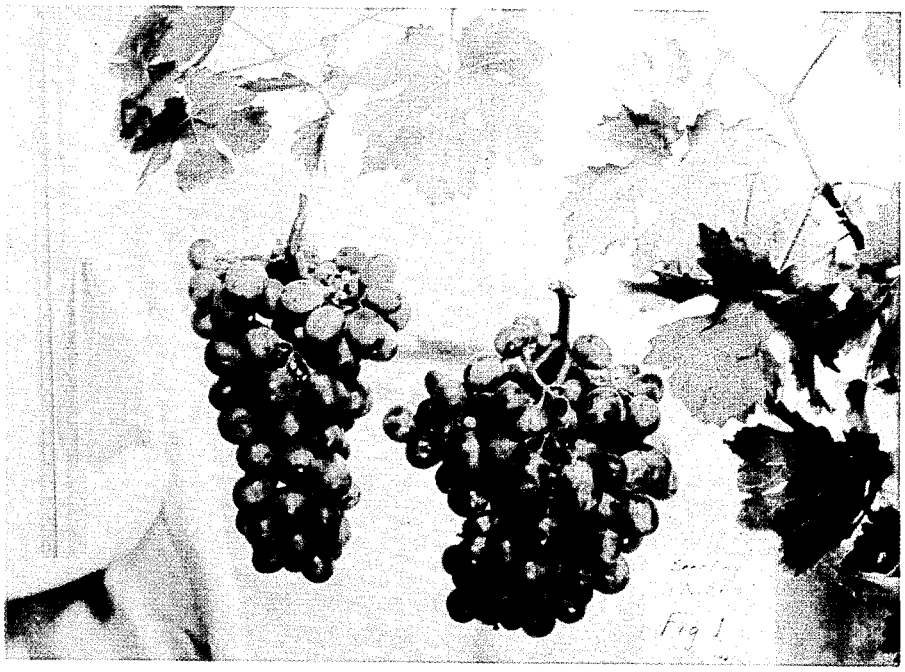
INVENTOR
MARVIN L. NIES
BY
TOWNSEND and TOWNSEND
Attorneys United States Patent Office Plant Pat. 2,345
Patented Jan. 21, 1964

2,345
GRAPEVINE

Marvin L. Nies, Rte. 1, P.O. Box 408, Lodi, Calif.

Filed Aug. 29, 1961, Ser. No. 134,790
1 Claim. (Cl. Plt.—47)

This invention relates to a new and distinct variety of grapevine obtained by crossing an unpatented seedling of Scolokerteck × Muscat Hamburg with an impatented seedling of Emperor × P.I. 75. Cuttings were taken at Lodi, California, in 1957 from the original seedlings employed. They were transferred to an area located a short distance southeast of Thermal, California, in Coachella Valley. At this latter location, the first fruit was obtained in 1959 and again in 1960. Observations reported here were made on the fruit of both years.

The predominant novel characteristics of this new variety of grapevine are that it has a bright red, somewhat ellipsoidal elongated berry under hot desert conditions and has early ripening fruit. In Thermal, California, the fruit matures with Perlette and before Cardinal under comparable conditions.

There is no existing early maturing variety that is similar to the presently claimed variety except the variety claimed in copending plant patent application 134,788 filed August 29, 1961. It is sufficient to state that the Cardinal berries are esssentially round and have a purple cast as compared with the present berries which are more ellipsoidal elongated in shape, smaller in size, and bright red in color. Further, whereas Cardinal has as a general condition very straggly clusters including many shot berries, the present variety is characterized generally by well filled bunches with little straggling and fewer shot berries.

The following is a detailed description of the new variety, with color terminology and plate reference in accordance with the Horticultural Colour Chart of the British Colour Council, except where general color terms of ordinary dictionary significance are obvious:

Vine: Moderately vigorous with no particular distinguishing aspects as to habit. General overall appearance of the vine is lacy due to the deep sinuses of the leaves.

Leaves:

*Blade.*—Palmate with well marked petiole sinus approximately ⅓ the length of the blade. The blade on the petiole sinus curves inwardly and on many leaves it is overlapping for complete closure of the petiole sinus. Inferior sinus well marked and slightly smaller than the superior sinus. Superior sinus extends approximately ½ way to the point where the blade attaches to the petiole. Leaf underside has very small hairs which are upright and stiff. Upper surface of the blade is glabrous.

*Color.*—Petiole lightly bronze tinged extending from the cane to the base of the veins on the blade. Veins generally light green and clearly marked. Terminal leaves of the shoot are Fern green, Plate 0862/1. Older leaves at base of the shoot are Spanish green, Plate 9060/1. Vigorous shoots exhibit slight bronzing between the veins of new leaves.

*Size.*—Average.

Fruit:

*Berry.*—Color (measured by natural light transmitted through excised skin): Chrysanthemum Crimson, Plate 824/3 with growing conditions at about 90° F. (average daytime maximum temperature) as the grapes approach maturity; hotter climatic conditions produce a shift toward Plate 8/22/3 to 8/22; uniform coloring. Size: average; 2.5 cm. in length and 2.25 cm. in width. Seeds: generally 2 or 3 per berry; about 7 mm. long and about 4–5 mm. wide; beak not pronounced; light green becoming brown with ripening. Shape: ellipsoidal elongated to rounded; some slightly flat or truncated on the end. Pulp: clear except for slight coloring on the tip of the brush tissue at 18° balling refractometer. Flavor: unique; very slight suggestion of Muscat flavor; normal acidity. Texture of flesh: crisp, firm to pressure and not juicy. Skin: relatively thin.

*Bloom.*—Very similar to most table grapes. Calyptras shedding completely, pollen abundant, fertile; ovary small.

*Pedical.*—Slender and about 1 cm. in length. Slight roughness.

*Torus.*—Not heavy. About 3–4 mm. in width.

*Brush.*—About 7 mm. long when pulled from the berry.

*Size of cluster.*—Medium to small. Normally from 20–30 cm. in length. Shoulder on less vigorous vines not pronounced. Approximately ¾–1½ lbs. without thinning.

*Period of ripening.*—Early; commences with Perlette. Extends to include the first Cardinals in Coachella Valley.

Uses: Fresh fruit is delightful eating. Principally intended as a table grape.

What is claimed is:

A new and distinct variety of grapevine, herein shown and described, characterized as to novelty by its bright red, somewhat rounded to ellipsoidal elongated berry, its unique flavor and early maturation date.

No references cited.